(12) United States Patent
Dehling

(10) Patent No.: US 10,946,142 B2
(45) Date of Patent: Mar. 16, 2021

(54) ADAPTER ELEMENT FOR FASTENING A NEEDLE TIP TO A SYRINGE BASE BODY

(71) Applicant: Gerresheimer Regensburg GmbH, Regensburg (DE)

(72) Inventor: Michael Dehling, Hahnbach (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 138 days.

(21) Appl. No.: 16/109,549

(22) Filed: Aug. 22, 2018

(65) Prior Publication Data

US 2019/0060574 A1 Feb. 28, 2019

(30) Foreign Application Priority Data

Aug. 24, 2017 (DE) .................. 10 2017 119 345

(51) Int. Cl.
*A61M 5/31* (2006.01)
*A61M 5/32* (2006.01)
*A61M 39/10* (2006.01)

(52) U.S. Cl.
CPC ........ *A61M 5/3134* (2013.01); *A61M 5/3293* (2013.01); *A61M 39/10* (2013.01); *A61M 2039/1077* (2013.01); *A61M 2207/00* (2013.01)

(58) Field of Classification Search
CPC .. A61M 5/34; A61M 5/3134; A61M 25/0014; A61M 5/3293; A61M 39/10; A61M 2039/1077; A61M 2207/00
See application file for complete search history.

(56) References Cited

U.S. PATENT DOCUMENTS

| | | | | |
|---|---|---|---|---|
| 2008/0051729 | A1* | 2/2008 | Cheng ................ | A61M 5/3272 604/232 |
| 2010/0292656 | A1* | 11/2010 | Groskopf ............ | A61M 5/3134 604/200 |
| 2013/0331799 | A1* | 12/2013 | Dasbach ............... | A61M 5/348 604/241 |
| 2014/0236102 | A1† | 8/2014 | Matsumoto | |

(Continued)

FOREIGN PATENT DOCUMENTS

| | | |
|---|---|---|
| CN | 101951981 A | 1/2011 |
| CN | 204337436 U | 5/2015 |

(Continued)

OTHER PUBLICATIONS

German Office Action, dated Apr. 16, 2018, corresponding to German Application No. 10 2017 119345.6 (filed Aug. 24, 2017), parent of the present application, 3 pp. (in German language).

(Continued)

*Primary Examiner* — Rebecca E Eisenberg
*Assistant Examiner* — John A Doubrava
(74) *Attorney, Agent, or Firm* — Leydig, Voit & Mayer, Ltd.

(57) ABSTRACT

The invention relates to an adapter element for fastening a needle element to a syringe base body, the adapter element having a base body which is configured and provided for receiving the needle element, the base body having at least one through-opening for passing the needle element through and for fixing it, and the base body being configured and provided for being fastened to the syringe base body.

14 Claims, 4 Drawing Sheets

(56) References Cited

U.S. PATENT DOCUMENTS

2015/0374931 A1* 12/2015 Sugiki .................. A61M 5/343
                                                    604/240
2016/0184558 A1*  6/2016 Raulerson ............. A61B 17/34
                                                    604/507

FOREIGN PATENT DOCUMENTS

| CN | 105188814 A   | 12/2015 |
|----|---------------|---------|
| EP | 2664550       | 11/2013 |
| JP | 2005-342100 A | 12/2005 |
| WO | 2009/090627   | 7/2009  |

OTHER PUBLICATIONS

Czech Office Action, dated Apr. 8, 2019, in Czech Patent Application No. PV 2018-423, a related application, 3 p. (with partial English translation).
Czech Search Report, dated Nov. 14, 2018, in Czech Patent Application No. PV 2018-423, a related application, 1 p.
China National Intellectual Property Administration, First Office Action and Search Report, dated Oct. 26, 2020, corresponding to Chinese Patent Application No. 201810961682.0, 18 pages.

\* cited by examiner
† cited by third party

ADAPTER ELEMENT FOR FASTENING A NEEDLE TIP TO A SYRINGE BASE BODY

CROSS-REFERENCE TO RELATED APPLICATIONS

This application is a U.S. Nonprovisional Application filed under 35 U.S.C. § 111(a) which claims the benefit of German Application No. 10 2017 1193 45.6, filed Aug. 24, 2017. This application is hereby incorporated by reference in its entirety.

BACKGROUND OF INVENTION

The present invention relates to an adapter element for fastening a needle element and/or a cannula to a syringe base body, to an adapter system for fastening a needle element to a syringe base body, and to a method for producing a needle element.

When needle elements are fastened to a syringe base body, the production process is complicated in particular as a result of the problem that needles of this type are only poorly suitable for direct integration into the syringe base body by insert molding or for adhesion thereto. This is due to, among other things, the small protrusion distance of a very short needle element of this type relative to the large-volume syringe base body. The large-volume syringe base body can therefore be positioned stably relative to the very short needle element only with difficulty.

It has further been found that gluing the needle element onto or into the syringe base body involves the risk of gas release from the curing glue. To prevent gas release of this type, in particular in the region of the short needle, a considerable effort must be made as regards checking the gluing if the glue is not to come into bodily contact with the user.

SUMMARY OF THE INVENTION

Therefore, from this starting point, an object of the present invention is, among other things, to provide an adapter element for fastening a needle element to a syringe base body which allows a particularly simple production method, in particular during the fastening of the needle element to the syringe base body. In addition, the present invention therefore offers design options with different adapters, depending on the secondary processes. The adapter element may, for example, also be configured and provided for use on the syringe base body in the case of laser welding, laser pressing, laser bonding and the like.

This object is achieved by the subject matter of claim 1.

The syringe base body may be part of a syringe and be formed as a cavity in which a piston body is movable to press the liquid for injection out of the syringe base body. However, a viscous or solid substance may be introduced into the syringe base body, in particular for pressing out using the piston body.

The needle element may be an injection needle. However, the use of a cannula instead of the needle element can also be considered.

In addition, an applicator is also conceivable instead of using a syringe base body.

In particular, the present invention therefore discloses, amongst other things, an adapter element for fastening a needle element to a syringe base body, the adapter element having a base body which is configured and provided for receiving the needle element, the base body having at least one through-opening for passing the needle element through and for fixing it. Further, the base body is configured and provided for being fastened to the syringe base body.

Therefore, according to the invention, a base body of this type is proposed which is used, in particular exclusively, in the field of medical syringes and medical injection systems. For example, the needle element can be passed through the through-opening in the base body in such a way that the needle element in particular only comes into contact with a rim of this through-opening. In other words, in an embodiment of this type, the needle element is in contact with the base body, in particular in mechanical contact, solely via the inner rim of the through-opening.

This may mean that the needle element is braced with respect to the base body in the through-opening. Preferably, a length of the base body in the longitudinal direction, in other words in the direction of a primary extension direction of the needle element and/or a direction parallel to the primary extension direction of the adapter element itself, is shorter than a length of the needle element. This can ensure that, once the needle element is mechanically connected to the adapter element via the through-opening, the ends of the needle element protrude out of the adapter element on both sides.

One of the major advantages of the present invention is therefore that a needle element no longer necessarily has to be gripped and fixed directly during a connection process to the syringe base body, but instead this can therefore take place indirectly via the adapter element. Specifically, by comparison with the surface of the needle element, the adapter element forms a much larger gripping area, in particular, among other reasons, also because the adapter element preferably completely encircles the needle in the radial direction. In other words, the adapter element is therefore preferably arranged around the needle element radially symmetrically with respect to the longitudinal direction.

In at least one embodiment, the adapter element for fastening a needle element to a syringe base body comprises a base body which is configured and provided for receiving the needle element, the base body having at least one through-opening for passing the needle element through and for fixing it, and the base body being configured and provided for being fastened to a syringe base body.

In at least one embodiment, the base body has at least one viewing opening extending through a wall element of the base body, in such a way that it is possible to see into an internal volume of the base body freely from the outside at least at points.

The viewing opening currently described is therefore to be understood as a wall aperture in the wall element, and provides the possibility of additionally fixing the needle tip, during mounting on the syringe base body, by means of a mounting which is to be inserted into the internal volume from the outside and which is to be passed through the viewing opening. After fixing of this type, the adapter element, together with a mounting end of the needle element opposite the needle tip, can be adhered to and/or cast on the syringe base body.

As briefly outlined previously above, the adapter element therefore not only allows simpler gripping of the needle tip, but also produces an enlargement of an area to be cast and/or adhered, greatly strengthening the connection between the needle element and the syringe base body. Preferably, after the casting and/or adhesion, the adapter element remains firmly on the syringe base body. A syringe produced in this manner therefore preferably likewise comprises the adapter element described herein.

In at least one embodiment, the base body has or is a hollow body, in particular a hollow cylinder. In this case, the needle element is passed through a bottom face and a top face of the base body, the wall element being a hollow wall element and in particular forming a hollow cylinder wall element, which laterally delimits, and in particular also encircles, the base body in the radial direction. The through-opening may be formed in the top face.

For example, the bottom face of the base body, opposite the top face in the longitudinal direction, is a purely virtual or imaginary bottom face. This may mean that in the longitudinal direction the base body is at least partially but preferably completely open proceeding from the top face towards the bottom face. Alternatively, however, the bottom face may also be a planar bottom element comprising a further through-opening formed therein. The top face may be a purely virtual or imaginary face.

However, it is also possible for the top face and/or the bottom face to be a face which is solid at least in parts, in other words formed with a haptically perceptible element, for example with the material of the base body. In this case, at least one of the through-openings described above may be formed in each of the top face and/or the bottom face. If a through-opening is formed both in the top face and in the bottom face, it is conceivable for the needle element to be in mechanical contact with the base body exclusively via the associated inner rim of this through-opening.

The formation of the base body, in particular as a hollow cylinder, therefore makes it possible to particularly simply mount the mounting end of the needle tip on the syringe base body.

In at least one embodiment, there is a cap region adjacent to a top face of the hollow body, a cap wall of the cap region having the through-opening. In this case, the top face is also at least in part, but preferably completely, a virtual or purely imaginary face which is laterally delimited by the wall element. This may mean that the hollow body is thus open on both sides in the longitudinal direction. Therefore, the cap wall of the cap region may be at least indirectly adjacent to the rim of the top face. The cap region may have or be a cap. The cap may be an element completely formed by the cap wall, which at least at points has an oblique and/or curved end face. It is conceivable for the through-opening to be positioned centrally through the point of least curvature of the cap. For example, the cap is formed as a dome. The cap may additionally be arranged rotationally symmetrically about the longitudinal direction. In other words, in this case, the centre line of the cap, and preferably also of the hollow body, is arranged on the longitudinal direction.

Preferably, the above-described viewing opening is different from the through-opening. For example, the through-opening is arranged exclusively in the cap region and the viewing opening is arranged exclusively in the base body. Preferably, a radial centre point of the through-opening is arranged on the longitudinal axis. The above-described viewing opening is therefore preferably arranged so as to be radially spaced from the longitudinal axis. The longitudinal axis preferably does not extend through the viewing opening, whilst for the through-opening, this is preferably the case.

In at least one embodiment, the cap wall is mechanically rigidly connected to the wall element. This may take place in that the wall is formed together with the wall element as in one piece, in particular as an injection molded element. This may mean that the adapter element is formed in an injection molding step, preferably a single injection molding step.

Alternatively or in addition, it is likewise conceivable for the adapter element described herein to be shaped in one or more blowing steps, in particular stretch-blowing steps.

Further, instead of the above-described one-piece configuration, it is conceivable for the cap element to be arranged detachably on the base body; this may mean that the cap element and the base body are detachably arranged on one another by means of locking clips or other holding elements. A plug-in or hook connection, by means of which the cap wall is detachably inserted into the wall element, is therefore likewise conceivable.

In this case, both the cap wall and the wall element of the hollow body comprise corresponding plug-in and/or hooking elements.

In at least one embodiment, an opening cross section of the through-opening corresponds at least to a needle cross section.

This may mean that the thickness of the needle element to be passed through the through-opening is less than the opening cross section of the through-opening itself, ensuring that the needle element is passed through the through-opening without difficulty, without undesired friction points or pressures occurring during passage.

In at least one embodiment, an opening cross section of the viewing opening is at least 1.5 times, preferably at least 2 times, as large as a needle cross section.

This ensures that the user can monitor and check the arrangement of the needle element within the adapter element from the outside during the mounting process at any time. In addition, a viewing opening created this large makes it possible to insert, with as little difficulty as possible, a corresponding holding element for fixing the needle tip during the connection process between the adapter element and the syringe base body.

For example, the adapter element is manufactured using the same material as the syringe base body. Plastics materials, such as a PET, are conceivable for this purpose.

Further, however, it is conceivable for an outer surface of the adapter element to be provided at least at points with a layer for increasing the static friction. This ensures, on the one hand, that, during handling of the adapter element, the user or the applied tool are at minimal risk of slipping off from the adapter element and, on the other hand, that during a gluing or casting process the casting material is applied to the outer layer of the adapter element with a particularly high coefficient of friction.

In at least one embodiment, an adapter system for fastening a needle element to a syringe base body is disclosed.

In this context, the adapter system described herein comprises an adapter element in accordance with at least one of the embodiments set out above. This means that all features disclosed in connection with the above-described adapter element are also disclosed for the adapter system described herein and vice versa.

The adapter system further comprises a needle element, the needle element being slid through the through-opening in the adapter element as far as a predeterminable length, in such a way that a needle tip region protrudes out of the adapter element.

Preferably, a mounting end opposite the needle tip region also protrudes out of the adapter element.

In the present case, the adapter system can be adhered and/or cast together with the syringe base body in one step.

The adapter element remains on the syringe base body constantly after the casting or adhesion.

The present invention further relates to a method for producing the needle element, comprising the steps whereby initially at least one adapter system in accordance with the above embodiment is provided, the adapter system being configured and provided for the needle element to be fastened to a syringe base body.

In a next step, the syringe base body is provided, the adapter system being connected to the syringe base body by at least one connection process, in particular by an injection molding process or a gluing process, in a further step.

All features disclosed for the adapter system described herein are also disclosed for the method described herein and vice versa.

Hereinafter, the invention is described in greater detail with reference to an embodiment and to the two associated drawings.

DETAILED DESCRIPTION OF THE INVENTION

Figure 1:
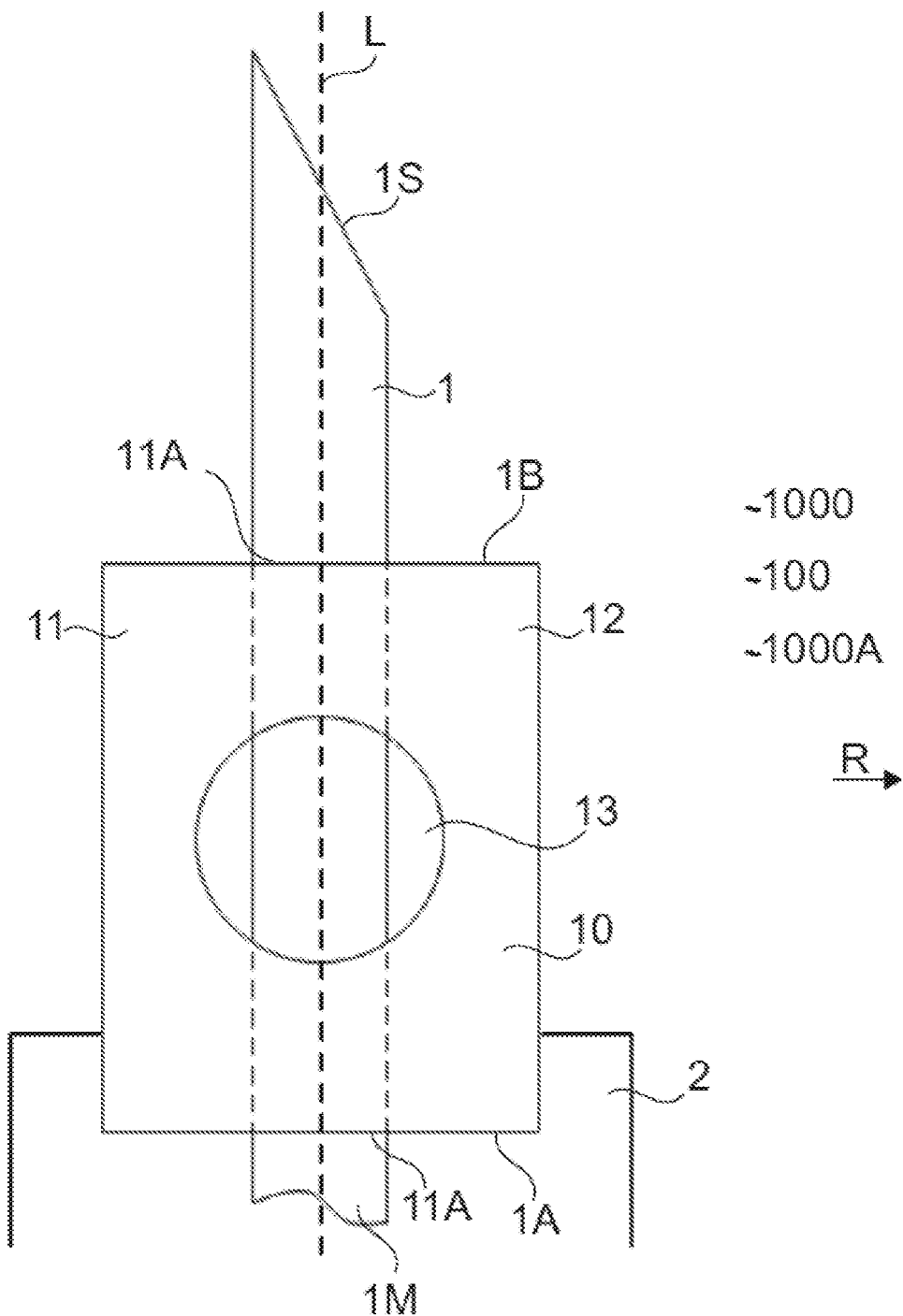
FIG. 1 and FIG. 2 show an embodiment of an adapter system 1000 according to the present invention which is fastened to a corresponding syringe base body 2, in each case in a schematic side view.

From FIG. 1, it can be seen that the adapter system 1000 shown therein comprises an adapter element 100 for fastening a needle element 1 to a syringe base body 2.

In this context, the needle element 1 has a needle tip region 1S, which is slid through a through-opening 11A in the adapter element 100 as far as a predetermined length of the needle element 1, in such a way that the needle element 1, at a predetermined length, comes into direct mechanical contact with the base body 10 of the adapter element 100 merely within the through-opening 11A.

In other words, the needle tip region 1S protrudes out of the adapter element 100. A mounting end 1M protrudes out of the base body 10 along the longitudinal direction L. In addition, it can also be seen that the base body 10 has a hollow body 11 in the form of a hollow cylinder, a bottom face 1A of the base body 10 also further protruding out of the mounting end 1M of the needle element 1.

The through-opening 11A is made in the top face 1B of the base body 10. The same applies to the bottom face 1A.

It is possible to see into the needle element 1 particularly clearly from the outside via a viewing opening 13 formed in the wall element 12 of the base body 10. Further, the viewing opening 13 is an opening configured and provided in such a way that a tool element for the needle element 1 can be passed through it and that the needle element 1 together with the adapter element 100 can be fastened to the syringe base body 2 without difficulty.

Therefore, a method as described herein can likewise be seen from FIG. 1, since the syringe base body 2 shown in FIG. 1 and the adapter system 1000 are interconnected by a gluing process (glued surface not shown here).

Figure 2:
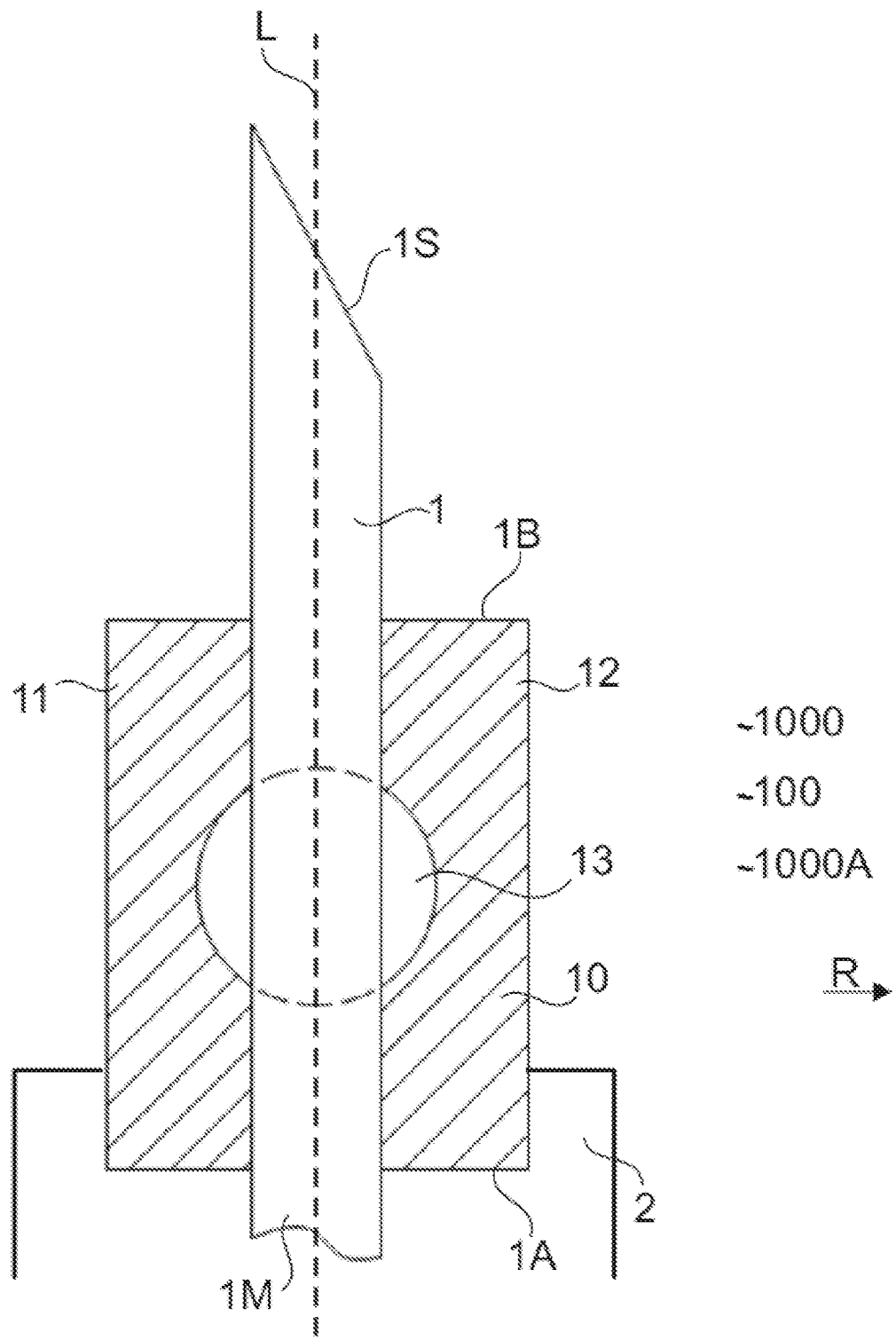

By contrast with FIG. 1, FIG. 2 shows the internal extension of the needle element 1 within the base body 10 again more clearly.

Figure 3:
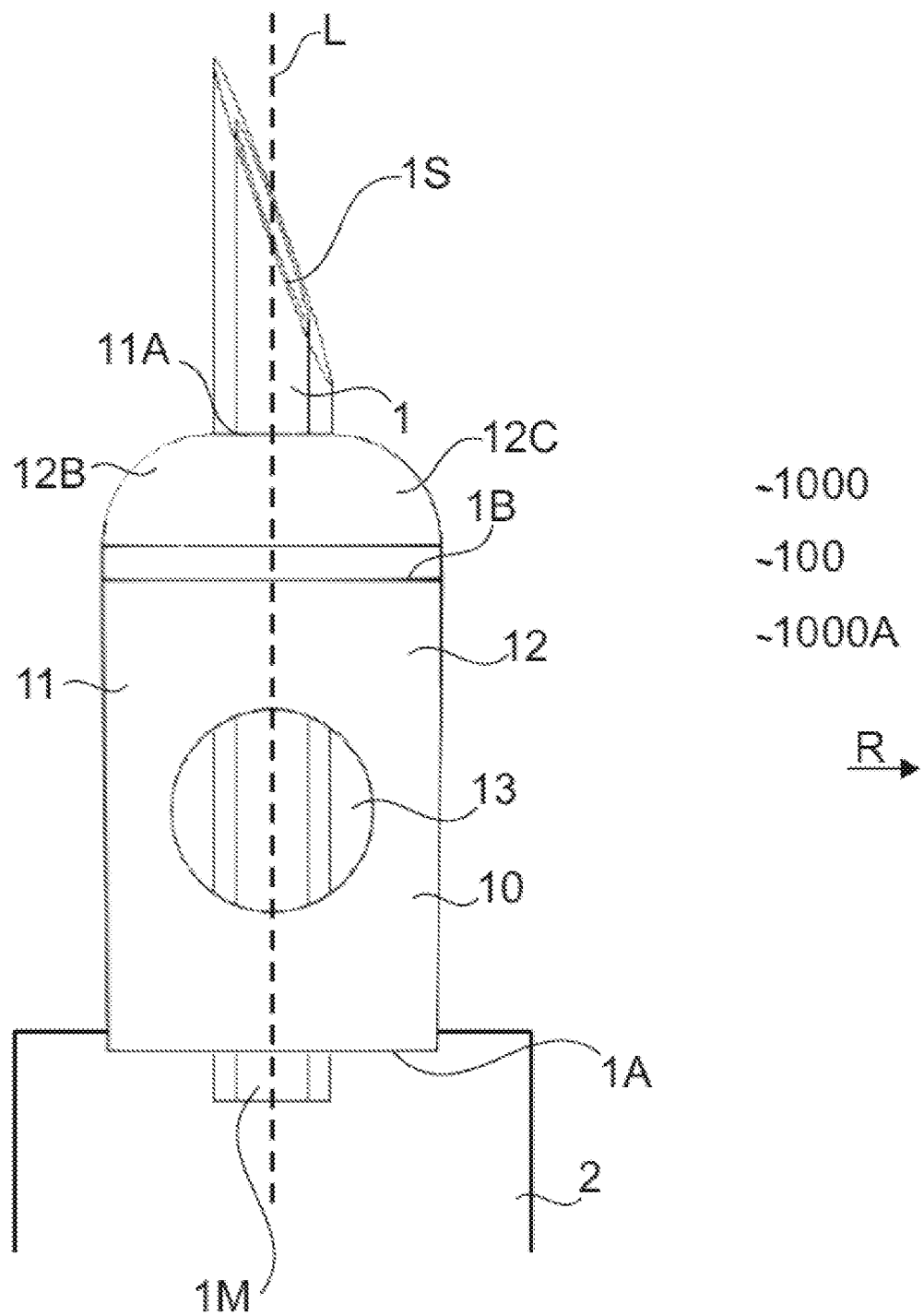
FIG. 3 and FIG. 4 each show a schematic side view of an embodiment of an adapter system 1000 having a cap adjacent to the top face of the hollow body.
Figure 4:
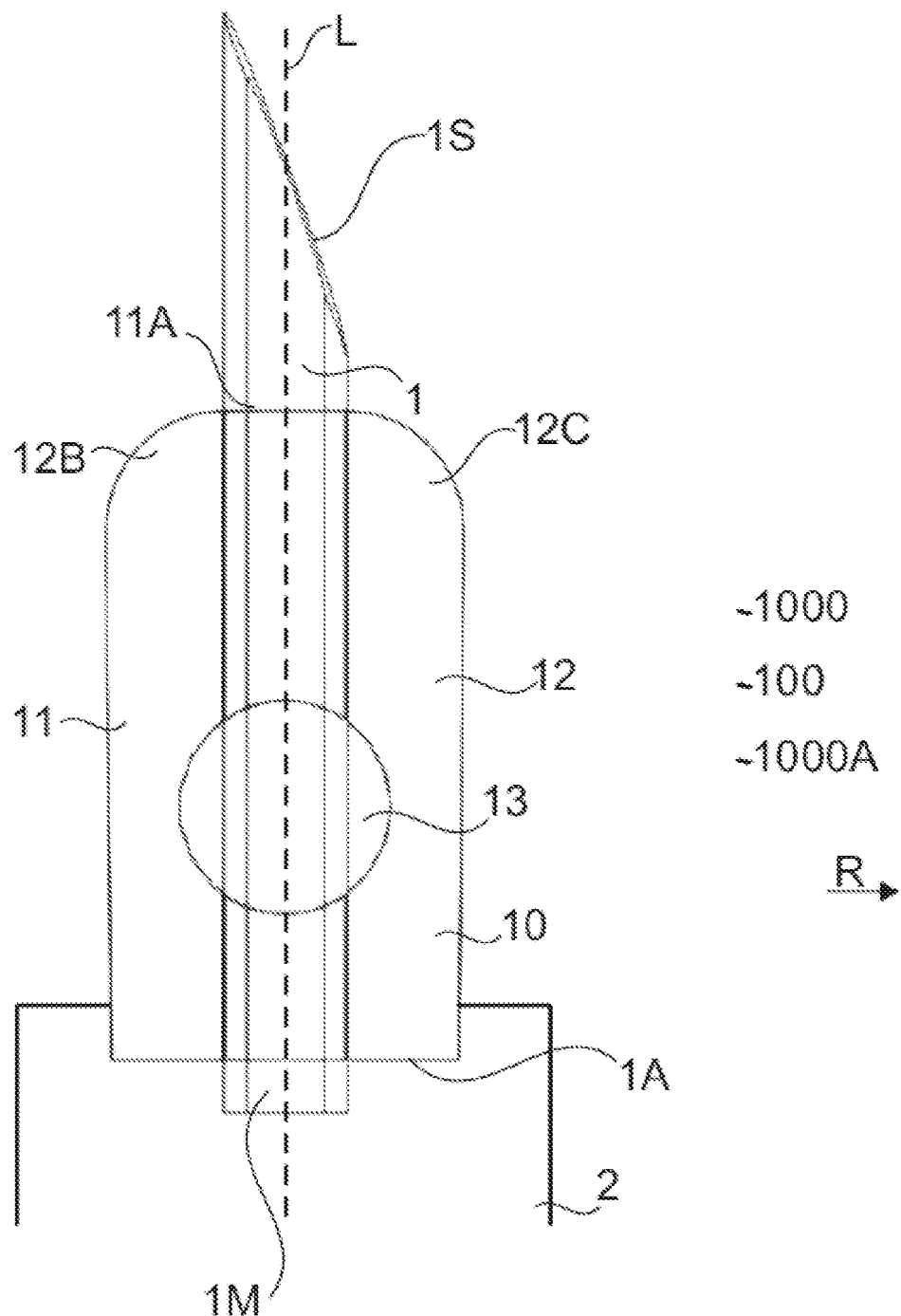

From FIG. 3 and FIG. 4, it can be seen that, by contrast with the embodiment of FIG. 1 and FIG. 2, there is a cap region 12C adjacent to the top face 1B of the hollow body 11, a cap wall 12B of the cap region 12C having the through-opening 11A. In this context, the top face 1B may be a purely virtual or imaginary face.

The invention is not limited by the description of embodiments. Rather, the invention comprises every novel feature and every combination of features, this also including in particular any combination of the claims, even if this feature or this combination is not itself explicitly disclosed in the claims and/or embodiments.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

LIST OF REFERENCE SIGNS

1 Needle element
1A Bottom face
1B Top face
1M Needle mounting region
1S Needle tip region
2 Syringe base body
10 Base body
11 Hollow body
11A Through-opening
12 Wall element
12B Cap wall
12C Cap region
13 Viewing opening
100 Adapter element
1000 Adapter system
1000A Method
L Longitudinal direction
R Radial direction

The invention claimed is:

1. An adapter element for fastening a needle element and/or a cannula to a syringe base body, comprising:
 a base body configured and provided for receiving the needle element,
 wherein the base body has at least one through-opening for passing the needle element through and for fixing the needle element,
 wherein the base body is configured and provided for being fastened to the syringe base body,
 wherein the base body comprises a hollow body and at least one viewing opening extending through a wall element of the hollow body, in such a way that it is possible to see into an internal volume of the hollow body freely from the outside at least in part,
 wherein the needle element passes through a bottom face of the hollow body, through the internal volume of the hollow body that is viewable through the at least one viewing opening, and through a top face of the hollow body; and
 wherein the at least one viewing opening is arranged along an axial direction between the bottom face of the hollow body and the top face of the hollow body.

2. The adapter element according to claim 1, wherein the wall element laterally delimits the base body in the radial direction (R).

3. The adapter element according to claim 1, wherein there is a cap region adjacent to the top face of the hollow body, a cap wall of the cap region having the through-opening.

4. The adapter element according to claim 1, wherein an opening cross section of the through-opening corresponds at least to a needle cross section.

5. The adapter element according to claim 1, wherein an opening cross section of the viewing opening is at least 1.5 times as large as a needle cross section.

6. An adapter system for fastening a needle element to a syringe base body, comprising
 an adapter element according to claim 1,
 a needle element, the needle element being slid through the through-opening in the adapter element as far as a predeterminable length, in such a way that a needle tip region protrudes out of the adapter element.

7. The adapter element of claim 2, where the hollow body is a hollow cylinder.

8. The adapter element according to claim 3, wherein the cap wall is mechanically rigidly connected to the wall element.

9. The adapter element according to claim 3, wherein the cap wall is a one-piece element together with the wall element.

10. The adapter element according to claim 9, wherein the cap wall is an injection molded element together with the wall element.

11. The adapter element of claim 5, where the opening cross section of the viewing opening is at least 2 times as large as a needle cross section.

12. A method for producing a syringe base body, comprising the steps of:
 providing at least one adapter system according to claim 1 for fastening the needle element to a syringe base body,
 providing the syringe base body, and
 fastening the adapter system to the syringe base body by at least one connection process.

13. The method of claim 12, wherein the connection process is a gluing process.

14. The method of claim 12, wherein the connection process is an injection molding process.

* * * * *